United States Patent [19]

Keiser et al.

[11] Patent Number: 5,053,199

[45] Date of Patent: Oct. 1, 1991

[54] ELECTRONICALLY READABLE INFORMATION CARRIER

[75] Inventors: Dale A. Keiser, Mesa; Charles A. Jackson, Sun City, both of Ariz.; William R. Boyd, Indianapolis, Ind.

[73] Assignee: Boehringer Mannheim Corporation, Indianapolis, Ind.

[21] Appl. No.: 313,244

[22] Filed: Feb. 21, 1989

[51] Int. Cl.[5] ...................... G01N 33/00; G01N 35/00
[52] U.S. Cl. ................................ 422/68.1; 422/82.01; 422/82.02; 439/70; 439/76; 439/260; 439/620
[58] Field of Search ...................... 422/55, 58, 63, 64, 422/65, 66, 68, 68.1, 82.01, 82.02; 439/70, 76, 260, 620

[56] References Cited

U.S. PATENT DOCUMENTS

| | | |
|---|---|---|
| D. 265,049 | 6/1982 | Flies . |
| D. 274,126 | 6/1984 | Flies . |
| D. 278,836 | 5/1985 | Flies . |
| D. 279,586 | 7/1985 | Flies . |
| D. 291,897 | 9/1987 | Flies . |
| 2,879,458 | 3/1959 | Schubert . |
| 2,929,042 | 3/1960 | Guttridge et al. . |
| 3,297,974 | 1/1967 | Pittman . |
| 3,345,541 | 10/1967 | Cobaugh et al. . |
| 3,408,612 | 10/1968 | Bute et al. . |
| 3,517,438 | 6/1970 | Johnson et al. . |
| 3,526,480 | 9/1970 | Findl et al. . |
| 3,551,295 | 12/1970 | Dyer . |
| 3,701,077 | 10/1972 | Kelly, Jr. . |
| 3,745,509 | 7/1973 | Woodward et al. . |
| 3,771,109 | 11/1973 | Bruckner et al. . |
| 3,794,469 | 2/1974 | Rapoza et al. ......................... 422/68 |
| 3,868,526 | 2/1975 | Caras . |
| 3,932,132 | 1/1976 | Hijikata . |
| 3,999,827 | 12/1976 | Hutchison et al. . |
| 4,023,879 | 5/1977 | Braund et al. ......................... 439/76 |
| 4,035,046 | 7/1977 | Kloth . |
| 4,179,178 | 12/1979 | Bachman et al. . |
| 4,216,522 | 8/1980 | Slagel et al. . |
| 4,297,569 | 10/1981 | Flies . |
| 4,326,125 | 4/1982 | Flies . |
| 4,327,953 | 5/1982 | Slagel et al. ........................... 339/17 |
| 4,329,642 | 5/1982 | Luthi et al. ............................ 339/17 |
| 4,379,966 | 4/1983 | Flies . |
| 4,406,508 | 9/1983 | Sadigh-Behzadi . |
| 4,436,993 | 3/1984 | Flies . |
| 4,464,832 | 8/1984 | Asick et al. ........................... 439/76 |
| 4,465,898 | 8/1984 | Orcutt et al. . |
| 4,480,835 | 11/1984 | Williams . |
| 4,490,001 | 12/1984 | Gordon et al. . |
| 4,491,378 | 1/1985 | Crawford . |
| 4,506,938 | 3/1985 | Madden . |
| 4,510,383 | 4/1985 | Ruppender . |
| 4,522,456 | 6/1985 | Wehrmacher . |
| 4,538,867 | 9/1985 | Wilson et al. . |

(List continued on next page.)

FOREIGN PATENT DOCUMENTS 132790A  2/1985  European Pat. Off. .

Primary Examiner—David L. Lacey
Assistant Examiner—Kimberly A. Trautman
Attorney, Agent, or Firm—Barnes & Thornburg

[57] ABSTRACT

An apparatus is provided in combination with an instrument for determining the concentration of a medically significant component of a biologically fluid. The apparatus includes an integrated circuit carrier and a socket for removably longitudinally receiving the integrated circuit carrier. The socket includes a first set of electrical contacts and the integrated circuit carrier includes a second set of electrical contacts positioned and arranged so as to be electrically contacted by respective contacts of the first set of electrical contacts. One of the integrated circuit carrier and socket includes upstanding first wall portions extending generally along the longitudinal length of one of the integrated circuit carrier and socket and lying generally between adjacent electrical contacts of the first set. The integrated circuit carrier further includes upstanding second wall portions extending between adjacent electrical contacts of the second set so as to reduce the likelihood of accidental electrical contact between adjacent electrical contacts of the second set.

4 Claims, 3 Drawing Sheets

U.S. PATENT DOCUMENTS

| | | |
|---|---|---|
| 4,549,036 | 10/1985 | Reichbach . |
| 4,549,076 | 10/1985 | Flies . |
| 4,560,218 | 12/1985 | Billman et al. . |
| 4,564,251 | 1/1986 | Hansen et al. . |
| 4,578,573 | 3/1986 | Flies et al. . |
| 4,598,962 | 7/1986 | Reitz et al. . |
| 4,609,240 | 9/1986 | Pistor . |
| 4,620,088 | 10/1986 | Flies . |
| 4,623,208 | 11/1986 | Kerul et al. . |
| 4,645,279 | 2/1987 | Grabbe et al. . |
| 4,648,665 | 3/1987 | Davis et al. ............................. 439/620 |
| 4,652,067 | 3/1987 | Lutzenberger . |
| 4,659,915 | 4/1987 | Flies . |
| 4,688,870 | 8/1987 | Egawa et al. . |
| 4,714,874 | 12/1987 | Morris et al. . |
| 4,752,679 | 6/1988 | Wehrmacher . |
| 4,766,520 | 8/1988 | Huber et al. ............................. 439/76 |
| 4,810,203 | 3/1989 | Komatsu ............................. 439/260 |

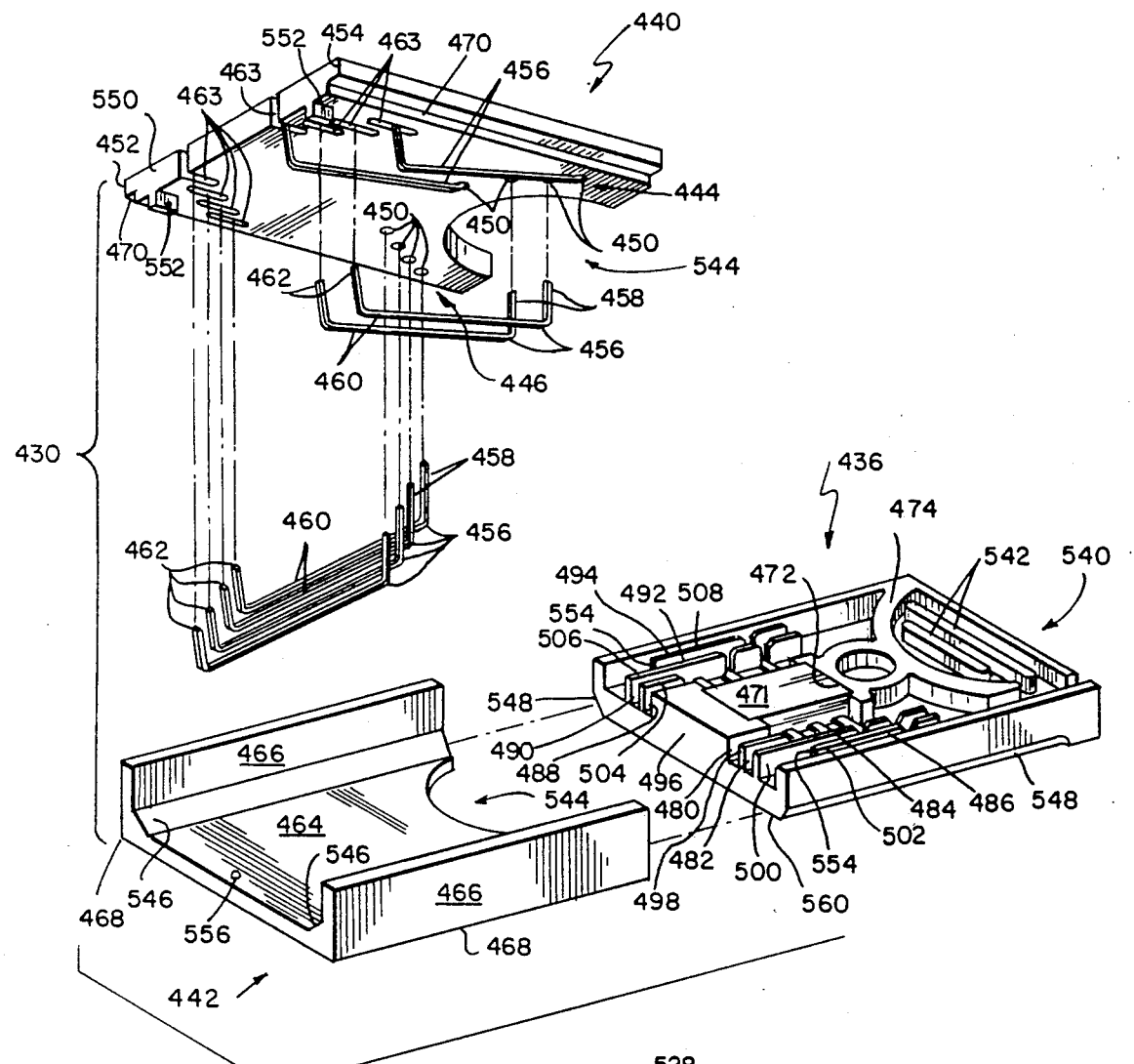
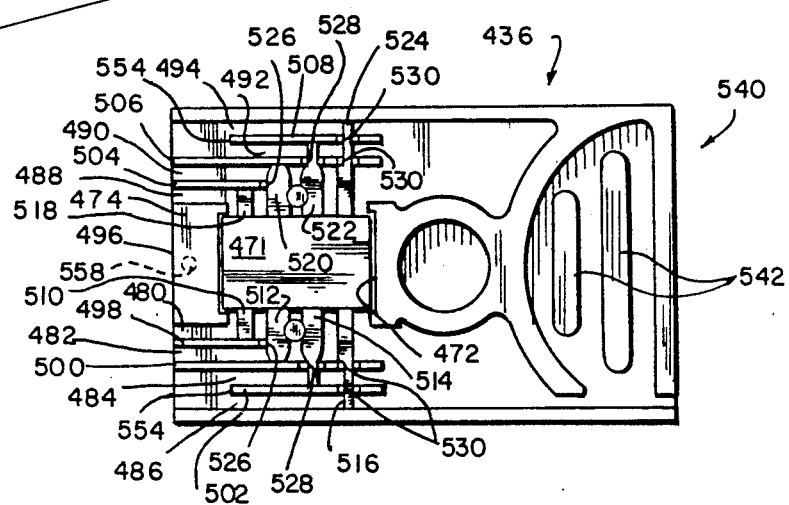

ELECTRONICALLY READABLE INFORMATION CARRIER

This invention relates to information carriers such as read-only-memory (ROM) integrated circuit chips, plug-in modules and the like. It is disclosed in the context of a clinical or diagnostic instrument. However, it is believed that the invention has utility in other fields as well.

Low-cost, disposable, electronically encoded information carriers have typically employed optical barcode (U.S. Pat. No. 4,510,383), magnetizable film (European Patent Application 132 790 A), perforated strip (U.S. Pat. No. 3,526,480), fluorogens which can be scanned by a fluorescent scanning device (U.S. Pat. No. 3,551,295), or electrically conductive medium on a carrier foil (U.S. Pat. No. 4,714,874) for imparting information which can be transmitted to instrumentation.

Higher cost, non-disposable information carriers utilizing memory integrated circuits have been employed in the video game and calculator industries in the form of printed circuit carriers and plastic cartridge enclosures. There is, for example, the system illustrated in U.S. Pat. No. 4,480,835.

In meters for calculating and displaying the results of reactions of medically significant components (e.g., glucose) of biological sera (e.g., blood, urine or the like) with test chemistries, it is well known that the test chemistries are not precisely reproducible from batch to batch. Similarly, the substrates which typically carry, or are impregnated with, the test chemistries can vary from batch to batch. If the results of reactions are to be determined visually or by optical means, slight differences in the colors of the substrates from batch to batch can cause errors in the interpretation of the results. In manual/visual interpretations, a chart typically is provided with each package of substrates impregnated with the test chemistry. This chart is prepared for the particular substrate/test chemistry combination in the package so that the likelihood of errors between the results embodied in the chart and the actual performance of the substrate/test chemistry in the package is very low.

However, many modern meters of the types described herein include automatic optical (e.g., reflectance) test chemistry readers which do not rely upon a person's ability to match, for example, the colors of reaction products on a test strip to colors on a chart provided with the package in which the test strip was supplied. Some reasons for the increased popularity of such automatic reading meters are clear. It is sometimes difficult for people whose sight is unimpaired to match colors on separate pieces of material, even ones placed side by side. Additionally many of the users of meters of the types described herein suffer from disorders such as diabetes which can impair their vision, sometimes severely. Yet they need to be able to monitor their blood glucose rather carefully.

Several currently popular automatic reading meters are provided with mechanisms by which certain calibration information, provided with each different package of test strips, can be entered by the user when each new package of test strips is purchased. This calibration information can be, for example, three data points on the reflectance curve generated by reagents of known concentration reacted with the test chemistry with which the test strips in the package are impregnated. Generally, entering this calibration information may be no more difficult than setting the time on a conventional digital watch. However, because the user may only use one package of test strips a month or so, the user typically will have to keep the instructions for entering the calibration information handy and refer to them every month or so to recalibrate the meter accurately.

It is a primary object of the present invention to provide an even simpler system for the calibration of meters of the types described herein. The invention contemplates that a read-only-memory or some other type of information carrier containing information pertinent to the optical characteristics of a particular batch of substrate/test chemistry be provided with each package of the substrate/test chemistry made up from that batch. Illustratively, the information carrier can be a disposable device. Alternatively, the information carrier can include erasable and programmable read-only-memory of some type which could be returned to the manufacturer of the substrate/test chemistry, erased and reprogrammed with information pertinent to a subsequent batch and recycled in this manner.

The invention may best be understood by referring to the following detailed descriptions of illustrative embodiments of the invention and the accompanying drawings of them. In the drawings:

FIG. 5 illustrates an exploded perspective view of another embodiment of the invention; and FIG. 6 illustrates a top plan view of the information carrier illustrated in FIG. 5.

Figure 1:
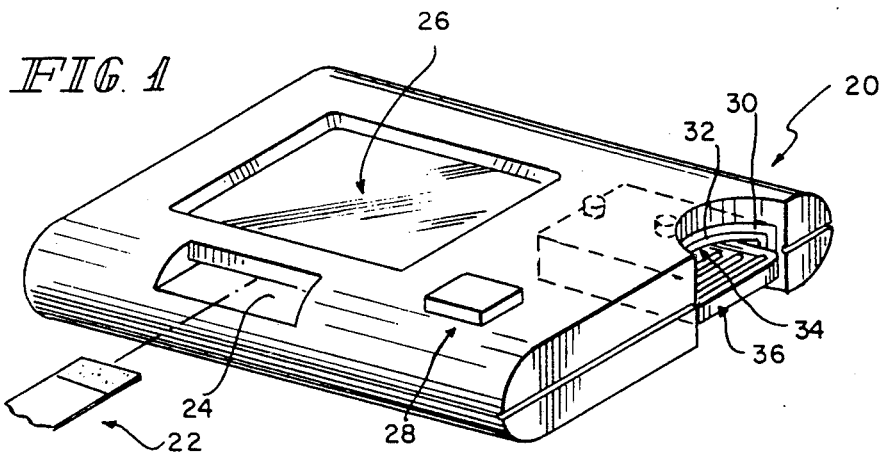
FIG. 1 illustrates a perspective view of an automatic reading meter of the type described herein, including the invention.

Referring to FIG. 1, an automatic reading blood glucose meter 20 for reading test strips 22 onto which droplets of blood have been placed is illustrated. Technologies and procedures for the placement of blood droplets on the strips 22, timing the reaction of the glucose in the blood droplets, and removing the blood from the strips 22 to halt the reaction of the glucose with the chemistries with which the strips 22 are treated are all well known and will not be discussed in any greater detail here. Meters of the type of described meter 20 are also well known and will not be further discussed here except to mention an example of such meters, the model ACCU-CHEK ® II meter available from Boehringer Mannheim Diagnostics, 9115 Hague Road, Indianapolis, Ind. 46250.

Meter 20 includes a slot 24 into which a reacted test strip 22 is inserted for reading, a display 26 and one or more buttons 28 which control the operation of the meter 20. The illustrated meter 20 also includes a socket 30 including an opening 32 accessible through one open end 34 of the socket 30 and into which information carriers 36 can selectively be inserted longitudinally. As previously mentioned, it is contemplated that an information carrier 36 carrying meter 20—calibrating information pertinent to a particular package of test strips 22 will be provided with that package of test strips. As the meter 20 executes its program each time a test strip 22 from that particular package is read, the calibration information will be read from the information carrier 36 by the meter 20 to enhance the accuracy of the meter 20's displayed result. When that package of test strips 22 is exhausted, the information carrier 36 can be discarded or returned to the manufacturer for reprogramming. A new information carrier 36 containing calibration information pertinent to a new package of test strips 22 will be provided with that new package of test strips 22.

Figure 2:
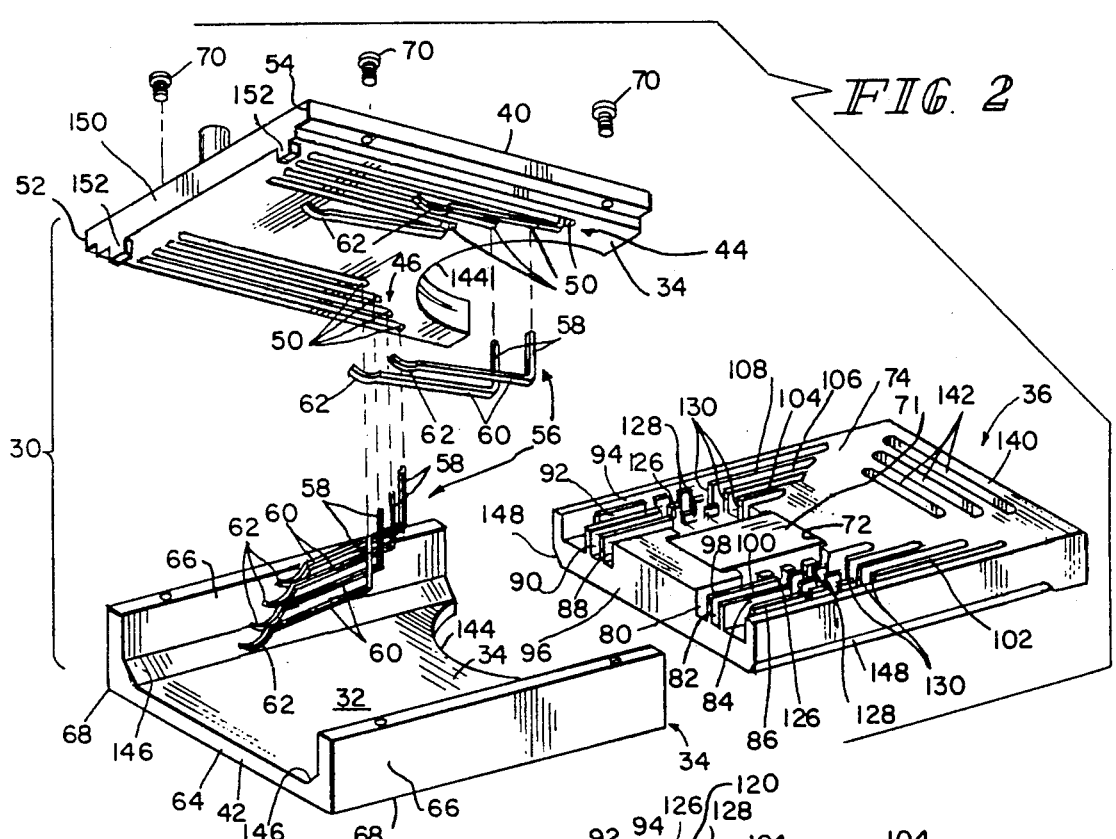
FIG. 2 illustrates an exploded perspective view of the embodiment of the invention illustrated in FIG. 1.
Figure 3:
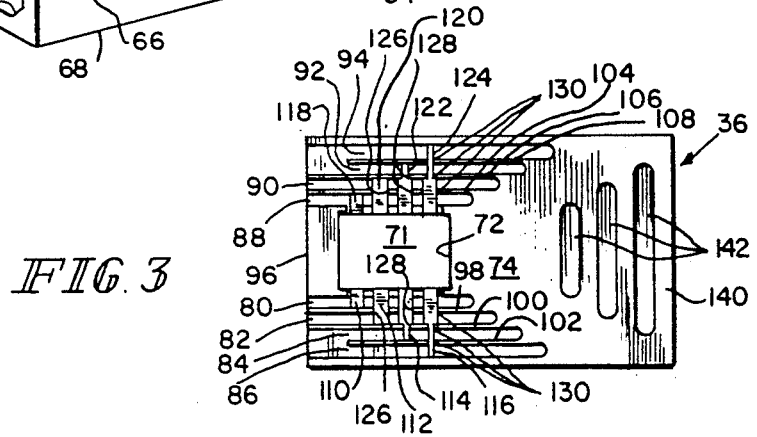
FIG. 3 illustrates a top plan view of the information carrier illustrated in FIGS. 1-2.

The configurations of the socket 30 and information carrier 36 are better illustrated in FIGS. 2-3. Both are illustratively constructed from high-impact injection molded resins. The socket 30 is constructed of an upper portion 40 and a lower portion 42. Upper portion 40 is provided with two diagonally extending rows 44, 46 of four openings 50 each. Row 44 is angled generally toward a corner 52 of upper portion 40 and row 46 is angled generally toward a corner 54 thereof. Eight substantially equal length, formed resilient wire, electrical contacts 56 include portions 58 which extend through respective openings 50 and portions 60 which extend rearwardly generally longitudinally of the socket 30, curving slightly downwardly and then upwardly adjacent their distal ends 62. The portions 58 can be connected to circuitry within meter 20 at the points at which they extend from socket upper portion 40. At their intersection, each portion 58 and 60 form between them an angle slightly greater than ninety degrees, for example, one hundred five degrees. Owing to this configuration and to the resiliency of the wire from which contacts 56 are constructed, the distal ends 62 of portions 60 are biased generally transversely of the longitudinal extent of socket 30 toward lower portion 42.

Lower portion 42 includes a bottom wall 64 and two longitudinally extending sidewalls 66 which extend perpendicularly upward from the opposite longitudinal edges 68 of bottom wall 64. The upper and lower portions 40, 42 of socket 30 are joined by screws 70 which project through openings provided therefor adjacent the corners of upper portion 40 and into respective, aligned threaded holes in the top edges of sidewalls 66.

Information carrier 36 includes an eight conductor (four conductors per side edge) read-only-memory integrated circuit chip 71 programmed with calibration information pertinent to a particular package of test strips. Chip 71 is mounted in a cavity 72 provided therefor in the upper surface 74 of carrier 36. Carrier 36 also includes grooves 80, 82, 84, 86, 88, 90, 92, 94 which extend longitudinally thereof and open into end wall 96 of carrier 36. Walls 98, 100, 102, 104, 106, 108 are thus formed between adjacent grooves 80, 82; 82, 84; 84, 86; 88, 90; 90, 92; and 92, 94, respectively. Grooves 80, 82, 84, 86, 88, 90, 92, 94 terminate along surface 74 of carrier 36 generally along the same diagonals as rows 44, 46 do along upper portion 40. The leads 110, 112, 114, 116, 118, 120, 122, 124 of chip 71 terminate in grooves 80, 82, 84, 86, 88, 90, 92, 94, respectively, with openings 126 being provided in walls 98, 104 for leads 112, 120, openings 128 being provided in walls 98, 100, 104, 106 for leads 114, 122, and openings 130 being provided in walls 98, 100, 102, 104, 106, 108 for leads 116, 124. Additional openings are illustrated in FIGS. 2-3 and can be provided. However, these additional openings need not be provided because leads 110, 112, 114, 116 and 118, 120, 122, 124 can be trimmed in the same diagonal patterns as rows 44, 46. Such diagonal trimming of leads 110, 112, 114, 116, 118, 120, 122, 124 further reduces the likelihood of inadvertent contact between electrical contacts 56 and the ones of leads 110, 112, 114, 116, 118, 120, 122, 124 with which respective contacts 56 are not to come into contact when carrier 36 is inserted fully into its use orientation in socket 30.

The outer end 140 of carrier 36 is provided with transversely extending grooves 142 which aid in gripping the carrier 36, for example, between the thumb and forefinger of the user for insertion of the carrier 36 into, and removal of carrier 36 from, socket 30. Semicircular cutouts 144 at the outer ends of upper and lower socket portions 40, 42 also aid insertion and removal. To help prevent insertion of carrier 36 into socket 30 upside down, a fillet 146 is provided at the base of each wall 66 of lower portion 42 where wall 66 joins bottom wall 64. Complementary chamfers 148 of a length sufficient to accommodate fillets 146 are provided along the bottom edges of carrier 36. The back or inner edge 150 of upper portion 40 is provided with downwardly extending tabs 152 which also help reduce the likelihood of overinsertion of carrier 36 into socket 30.

Figure 4:
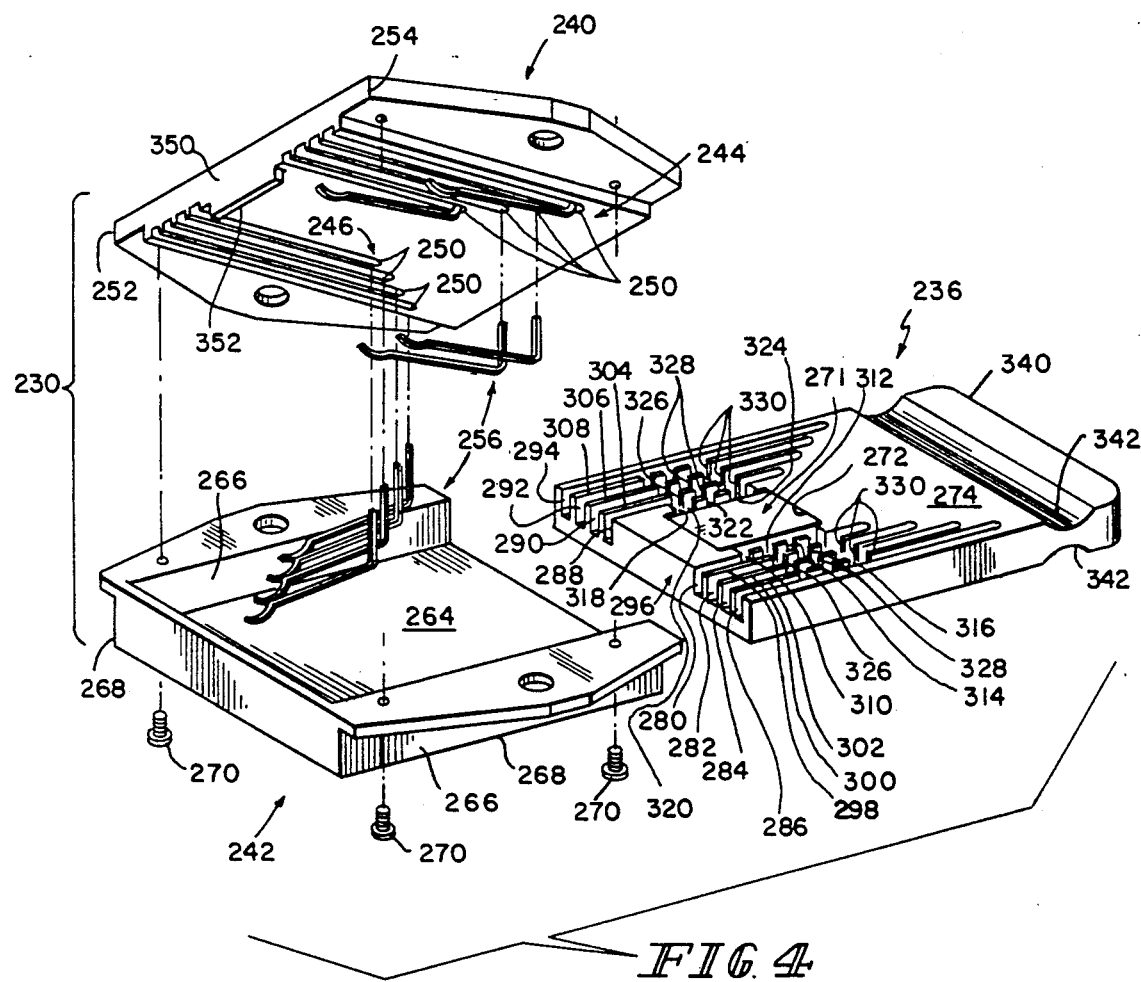
FIG. 4 illustrates an exploded perspective view of another embodiment of the invention.

Another configuration of the socket and information carrier is illustrated in FIG. 4. The socket 230 is constructed of an upper portion 240 and a lower portion 242. Upper portion 240 is provided with two diagonally extending rows 244, 246 of four openings 250 each. Row 244 is angled generally toward a corner 252 of upper portion 240 and row 246 is angled generally toward a corner 254 thereof. Eight substantially equal length, formed resilient wire, electrical contacts 256 of substantially the same configuration as contacts 56 in the embodiment of FIGS. 2-3 are mounted in respective openings 250.

Lower portion 242 includes a bottom wall 264 and two longitudinally extending sidewalls 266 which extend perpendicularly upward from the opposite longitudinal edges 268 of bottom wall 264. The upper and lower portions 240, 242 of socket 230 are joined by screws 270 which project through openings provided therefor adjacent the corners of lower portion 242 and into respective, aligned threaded holes in the upper portion 240.

Information carrier 236 includes an eight conductor (four conductors per side edge) read-only-memory integrated circuit chip 271 programmed with calibration information pertinent to a particular package of test strips. Chip 271 is mounted in a cavity 272 provided therefor in the upper surface 274 of carrier 236. Carrier 236 also includes grooves 280, 282, 284, 286, 288, 290, 292, 294 which extend longitudinally thereof and open into end wall 296 of carrier 236. Walls 298, 300, 302, 304, 306, 308 are thus formed between adjacent grooves 280, 282; 282, 284; 284, 286; 288, 290; 290, 292; and 292, 294, respectively. Grooves 280, 282, 284, 286, 288, 290, 292, 294 terminate along surface 274 of carrier 236 generally along the same diagonals as rows 244, 246 do along upper portion 240. The leads 310, 312, 314, 316, 318, 320, 322, 324 of chip 271 terminate in grooves 280, 282, 284, 286, 288, 290, 292, 294, respectively, with openings 326 being provided in walls 298, 304 for leads 312, 320, openings 328 being provided in walls 298, 300, 304, 306 for leads 314, 322, and openings 330 being provided in walls 298, 300, 302, 304, 306, 308 for leads 316, 324. Additional openings are illustrated in FIG. 4 and can be provided. However, these additional openings need not be provided because leads 310, 312, 314, 316 and 318, 320, 322, 324 can be trimmed in the same diagonal patterns as rows 244, 246. Such diagonal trimming of leads 310, 312, 314, 316, 318, 320, 322, 324 further reduces the likelihood of inadvertent contact between electrical contacts 256 and the ones of leads 310, 312, 314, 316, 318, 320, 322, 324 with which respective contacts 256 are not to come into contact when carrier 236 is inserted fully into its use orientation in socket 230.

The outer end 340 of carrier 236 is provided with transversely extending grooves 342 which aid in gripping the carrier 236, for example, between the thumb and forefinger of the user for insertion of the carrier 236 into, and removal of carrier 236 from, socket 230. The back or inner edge 350 of upper portion 240 is provided with a downwardly extending tab 352 which helps reduce the likelihood of overinsertion of carrier 236 into socket 230.

Referring to FIGS. 5-6, a socket 430 is constructed of an upper portion 440 and a lower portion 442. Upper portion 440 is provided with two diagonally extending rows 444, 446 of four openings 450 each. Row 444 is angled generally toward a corner 452 of upper portion 440 and row 446 is angled generally toward a corner 454 thereof. Eight substantially equal length, formed resilient wire, electrical contacts 456 include portions 458 which extend through respective openings 450 and portions 460 which extend rearwardly generally longitudinally of the socket 430, and then extend upward adjacent their distal ends 462 through respective elongated, longitudinally extending slots 463 provided in upper portion 440 of socket 430. The portions 458 can be connected to circuitry within a meter at the points at which they extend from socket upper portion 440. At their intersection, each portion 458 and 460 form between them an angle slightly greater than ninety degrees, for example, one hundred five degrees. Owing to this configuration and to the resiliency of the wire from which contacts 456 are constructed, the distal ends 462 of portions 460 are biased generally transversely of the longitudinal extent of socket 430 toward lower portion 442.

Lower portion 442 includes a bottom wall 464 and two longitudinally extending sidewalls 466 which extend perpendicularly upward from the opposite longitudinal edges 468 of bottom wall 464. The upper and lower portions 440, 442 of socket 430 are joined by ultrasonically welding them together at regions 470 of upper portion 440 and along the top edges of sidewalls 466.

Information carrier 436 includes an eight conductor (four conductors per side edge) read-only-memory integrated circuit chip 471 programmed with calibration information pertinent to a particular package of test strips. Chip 471 is mounted in a cavity 472 provided therefor in the upper surface 474 of carrier 436. Carrier 436 also includes grooves 480, 482, 484, 486, 488, 490, 492, 494 which extend longitudinally thereof and open into end wall 496 of carrier 436. Walls 498, 500, 502, 504, 506, 508 are thus formed between adjacent grooves 480, 482; 482, 484; 484, 486; 488, 490; 490, 492; and 492, 494, respectively. Grooves 480, 482, 484, 486, 488, 490, 492, 494 open at their other ends into a web region of carrier 436. The leads 510, 512, 514, 516, 518, 520, 522, 524 of chip 471 terminate in grooves 480, 482, 484, 486, 488, 490, 492, 494, respectively, with walls 498, 504 terminating at 526 for leads 512, 520, openings 528 being provided in walls 500, 506 for leads 514, 522, and openings 530 being provided in walls 500, 502, 506, 508 for leads 516, 524. Leads 510, 512, 514, 516 and 518, 520, 522, 524 are trimmed in the same diagonal patterns as rows 444, 446. Such diagonal trimming of leads 510, 512, 514, 516, 518, 520, 522, 524 further reduces the likelihood of inadvertent contact between electrical contacts 456 and the ones of leads 510, 512, 514, 516, 518, 520, 522, 524 with which respective contacts 456 are not to come into contact when carrier 436 is inserted fully into its use orientation in socket 430.

The outer end 540 of carrier 436 is provided with transversely extending bosses 542 which aid in gripping the carrier 436, for example, between the thumb and forefinger of the user for insertion of the carrier 436 into, and removal of carrier 436 from, socket 430. Semicircular cutouts 544 at the outer ends of upper and lower socket portions 440, 442 also aid insertion and removal. To help prevent insertion of carrier 436 into socket 430 upside down, a fillet 546 is provided at the base of each wall 466 of lower portion 442 where wall 466 joins bottom wall 464. Complementary chamfers 548 of a length sufficient to accommodate fillets 546 are provided along the bottom edges of carrier 436. The back or inner edge 550 of upper portion 440 is provided with downwardly extending tabs 552 which engage the inner ends 554 of walls 502, 508 to reduce the likelihood of overinsertion of carrier 436 into socket 430. A boss 556 which projects upwardly from the bottom wall 464 of lower portion 442 of socket 430 and a complementary recess 558 on the underside 560 of carrier 436 near the inner end thereof help identify for the user when the carrier 436 is in the use orientation.

It will thus be appreciated that, according to the invention, a standard multiple-sourced, commercially available integrated circuit is modified by automated machinery and inserted into a single, low-cost, mass producible, injection molded plastic carrier in such a manner as to provide electrostatic discharge protection, with the IC leads oriented for contact by a plurality of electrical contacts in a mating socket which typically is mounted on a printed circuit board.

The information carrier package of the present invention is a single piece, low cost, mass producible, injection molded plastic part. Previous designs have utilized multiple parts, materials, and complex manufacturing processes. The integrated circuit used is packaged in an industry standard dual in-line package, which is installed in the carrier by means of a low cost method, for example, press-fitting, as opposed to the traditional solder-in-place method, or custom-manufactured integrated circuits. The carrier design affords electrostatic discharge protection to the IC, a feature not available in open contact designs, and at less cost and complexity than shutter-type devices. The capacity or function of the unit can be easily changed by installing a different IC into the carrier. Data transfer with the device is by means of the simplest digital interface, permitting its use in low-cost, portable, battery-operated instruments. The present invention provides direct contact between a chip and the meter I/O. Most of the prior art puts the chip on a printed circuit board which is in turn connected with the computer. The present invention provides wiping contact between the chip I/O and the meter I/O. The prior art mostly involves game cartridges or special program cartridges for hand-held computers. The program cartridges or game cartridges typically have male contacts on the edge of a printed circuit board which communicate with female contacts in the body of the game or computer. Normally, there is no direct contact between the chip and the computer. Most prior art techniques require the use of complex reading electronics such as optical or magnetic readers and correspondingly complex software algorithms. The information storage density with the present invention is higher than most competing technologies. These differences permit application of the device as a disposable information carrier, not previously realizable because of higher prior art costs.

What is claimed is:

1. In combination, an apparatus comprising an integrated circuit carrier means for carrying an integrated circuit and a socket means for removably receiving the carrier means and through which electrical contact is made to the integrated circuit to provide communication with the integrated circuit when the carrier means is inserted into its use orientation in the socket means, the socket means including an opening constructed so as to slidably longitudinally receive the carrier means and a first set of electrical contacts, the carrier means including a second set of electrical contacts positioned and arranged so as to be electrically contacted by respective contacts of the first set, at least one of the socket means and carrier means also comprising upstanding first wall portions extending along the longitudinal length of at least one of the socket means and carrier means to promote separation of the electrical contacts of the first set from each other when the carrier is received in the socket means, the carrier means comprising upstanding second wall portions extending between adjacent electrical contacts of the second set of electrical contacts so as to reduce the likelihood of accidental electrical contact between adjacent electrical contacts of the second set.

2. In combination with an instrument means for determining the concentration of a medically significant component of a biological fluid by determining a characteristic of a product of a reaction of the medically significant component with a test chemistry, an apparatus comprising an integrated circuit carrier means for carrying an integrated circuit containing information relating to the test chemistry to calibrate the instrument means to determine the concentration of the medically significant component more accurately, and a socket means for removably receiving the carrier means and through which electrical contact is made to the integrated circuit to provide the calibration information to the instrument means when the carrier means is inserted into its use orientation in the socket means, the socket means including an opening constructed so as to slidably longitudinally receive the carrier means and a first set of electrical contacts, the carrier means including a second set of electrical contacts positioned and arranged so as to be electrically contacted by respective contacts of the first set of electrical contacts, one of the carrier means and socket means including means comprising upstanding first wall portions extending generally along the longitudinal length of one of the carrier means and socket means and lying generally between adjacent electrical contacts of the first set to promote separation of the adjacent electrical contacts of the first set from each other when the carrier means is received in the socket means, and the carrier means including means comprising upstanding second wall portions extending between adjacent electrical contacts of the second set so as to reduce the likelihood of accidental electrical contact between adjacent electrical contacts of the second set.

3. In combination, an apparatus comprising an integrated circuit carrier means for carrying an integrated circuit and a socket means for removably receiving the carrier means and through which electrical contact is made to the integrated circuit to provide communication with the integrated circuit when the carrier means is inserted into its use orientation in the socket means, the socket means including an opening constructed so as to slidably longitudinally receive the carrier means and a plurality of first electrical contacts which extend along the longitudinal length of the socket means, said plurality of first electrical contacts being biased to project transversely into the opening to facilitate contact with a plurality of second electrical contacts on the carrier means, the carrier means including said plurality of second electrical contacts, said plurality of second electrical contacts extending generally transversely to said plurality of first electrical contacts, at least one of the socket means and carrier means also comprising upstanding first wall portions extending generally along the longitudinal length of at least one of the socket means and carrier means so that said first wall portions will lay generally between adjacent ones of said plurality of first electrical contacts when the carrier means is fully inserted into a use orientation in the socket means to promote separation of the plurality of first electrical contacts from each other during insertion of the carrier means into, removal of the carrier means from, and while the carrier means is in its use orientation in the socket means, and the carrier means including means comprising second wall portions between adjacent ones of said plurality of second electrical contacts so as to reduce the likelihood of accidental contact between adjacent ones of said plurality of second electrical contacts.

4. In combination, an apparatus comprising an integrated circuit means for carrying an integrated circuit and a socket means for removably receiving the carrier means and through which electrical contact is made to the integrated circuit to provide communication with the integrated circuit when the carrier means is inserted into it use orientation in the socket means, the socket means including an opening constructed so as to slidably longitudinally receive the carrier means and a plurality of first electrical contacts which extend longitudinally along the longitudinal length of the socket means, said plurality of first electrical contacts being biased to project transversely into the opening to facilitate contact with second electrical contacts provided on the carrier means, the carrier means including a plurality of said second electrical contacts, the carrier means also comprises upstanding first wall portions extending generally along the longitudinal length of the carrier means so that said first wall portions will lay generally between adjacent ones of said plurality of first electrical contacts when the carrier means is fully inserted into a use orientation in the socket means to promote separation of the plurality of first electrical contacts from each other during insertion of the carrier means into, removal of the carrier means from, and while the carrier means is in its use orientation in the socket means, and the carrier means including means comprising second wall portions extending between adjacent said second electrical contacts to reduce the likelihood of accidental contact between adjacent said second electrical contacts.

* * * * *